(12) United States Patent
Pandya et al.

(10) Patent No.: US 12,073,483 B1
(45) Date of Patent: Aug. 27, 2024

(54) SYSTEMS AND METHODS FOR MULTIDIMENSIONAL ACCESS SYSTEM FOR DISTRIBUTED SITES

(71) Applicant: Morgan Stanley Services Group Inc., New York, NY (US)

(72) Inventors: Ankit Pandya, Monmouth Junction, NJ (US); David E. Stark, New York, NY (US); Wallace Gobetz, West Orange, NJ (US); James Carter, Garbet Valley, PA (US); Srinivas Alladi, Princeton Junction, NJ (US); Stephan M. Gharibian, Wayne, NJ (US)

(73) Assignee: Morgan Stanley Services Group Inc., New York, NY (US)

( * ) Notice: Subject to any disclaimer, the term of this patent is extended or adjusted under 35 U.S.C. 154(b) by 0 days.

(21) Appl. No.: 18/323,081

(22) Filed: May 24, 2023

(51) Int. Cl.
| | |
|---|---|
| *G06Q 50/26* | (2024.01) |
| *G07C 9/25* | (2020.01) |
| *G07C 9/27* | (2020.01) |
| *G16H 10/20* | (2018.01) |
| *G16H 10/65* | (2018.01) |
| *G16H 20/10* | (2018.01) |
| *G16H 50/80* | (2018.01) |

(52) U.S. Cl.
CPC .............. *G06Q 50/265* (2013.01); *G07C 9/25* (2020.01); *G07C 9/27* (2020.01); *G16H 10/20* (2018.01); *G16H 10/65* (2018.01); *G16H 20/10* (2018.01); *G16H 50/80* (2018.01)

(58) Field of Classification Search
CPC ........ G16H 10/60; G16H 10/40; G16H 50/30; G16H 50/80
See application file for complete search history.

(56) References Cited

U.S. PATENT DOCUMENTS

| | | | |
|---|---|---|---|
| 11,342,051 B1 * | 5/2022 | Jain | G16H 10/60 |
| 11,625,964 B2 * | 4/2023 | Rajamanickam | A61B 5/6889 340/5.2 |
| 2014/0167917 A2 | 6/2014 | Wallace et al. | |
| 2021/0361240 A1 * | 11/2021 | Fialkov | G16H 50/80 |
| 2021/0390812 A1 * | 12/2021 | Chaurasia | G07C 9/20 |
| 2021/0391041 A1 * | 12/2021 | White | H04L 63/102 |
| 2022/0027816 A1 | 1/2022 | Ritter et al. | |

(Continued)

FOREIGN PATENT DOCUMENTS

WO WO-2021231377 A1 * 11/2021

OTHER PUBLICATIONS

Davoodi M, Senapati A, Mertel A, Schlechte-Welnicz W, M Calabrese J. On the optimal presence strategies for workplace during pandemics: A COVID-19 inspired probabilistic model. PLoS One. May 12, 2023;18(5):e0285601. doi: 10.1371/journal.pone.0285601. PMID: 37172012; PMCID: PMC10180602 (Year: 2023).*

(Continued)

*Primary Examiner* — Joseph D Burgess (74) *Attorney, Agent, or Firm* — PEARL COHEN ZEDEK LATZER BARATZ LLP (57) ABSTRACT

Systems and methods for remote badging and/or computer access, automatic individual verification, automatic vaccine verification and/or automatically remotely determining an individual's physical presence at a site are provided. The systems and methods include automatic vaccine proof verification.

12 Claims, 7 Drawing Sheets

(56) References Cited

U.S. PATENT DOCUMENTS

| | | | |
|---|---|---|---|
| 2022/0028561 A1 | 1/2022 | Klasson | |
| 2022/0222995 A1* | 7/2022 | Adur | G07C 9/27 |
| 2022/0301667 A1* | 9/2022 | Church | G16H 40/20 |

OTHER PUBLICATIONS

Davoodi M, Senapati A, Mertel A, Schlechte-Welnicz W, M Calabrese J. On the optimal presence strategies for workplace during pandemics: A COVID-19 inspired probabilistic model. PLOS One. May 1, 20232; 18(5):e0285601. doi: 10.1371/journal.pone.0285601 PMID: 37172012; Pmcid: PMC10180602 (Year: 2023).*

Standardized surveillance case definition and national notification for 2019 novel coronavirus disease (COVID-19), Interim-20-ID-01, Infectious Disease, CSTE, Council of State and Territorial Epidemiologists, 2019, 10 pgs.

Interim Guidance on Developing a COVID-19 Case Investigation & Contact Tracing Plan: Overview, Centers for Disease Control and Prevention, downloaded from https://www.cdc.gov/coronavirus/2019-ncov/php/contact-tracing/contact-tracing-plan/overview.html, Feb. 28, 2022, 3 pgs.

Public health surveillance for COVID-19: interim guidance, Interim guidance, Jul. 22, 2022, World Health Organization, COVID-19: Surveillance, case investigation and epidemiological protocols, downloaded from https://www.who.int/publications/1/item/who-2019-nCoV-surveillanceguidance-2020.7 , 33 pgs.

Human Infection with 2019 Novel Coronavirus Case Report Form, Centers for Disease Control and Prevention, CDC 2019-nCOV ID, downloaded from https://www.cdc.gov/coronavirus/2019-ncov/downloads/pui-form.pdf ,2pgs.

Revised case report form for Confirmed Novel Coronavirus COVID-19 (report to WHO within 48 hours of case identification), World Health Organization, downloaded from https://apps.who.int/iris/bitstream/handle/10665/331234/WHO-2019-nCoV-SurveillanceCRF-2020.2-eng.pdf, Feb. 27, 2020, 3 pgs.

Digital Contact Tracing Tools, Centers for Disease Control and Prevention, COVID-19, May 26, 2020, downloaded from https://www.cdc.gov/coronavirus/2019-ncov/php/contact-tracing/contact-tracing-plan/digital-contact-tracing-tools.html , 4 pgs.

Contact Tracing for COVID-19, Centers for Disease Control and Prevention, COVID-19, Feb. 10, 2022, downloaded from https://www.cdc.gov/coronavirus/2019-ncov/php/contact-tracing/contact-tracing-plan/contact-tracing.html , 8 pgs.

Contact Tracing in the Context of COVID-19, World Health Organization, Interim Guidance Feb. 1, 2021, downloaded from WHO-2019-nCoV-Contact_Tracing-2021.1-eng.pdf , 11 pgs.

Guidance for the New York State COVID-19 Vaccination Program: Vaccination of Individuals Ages 6 Months to Adult, NYS Dept of Health, https://coronavirus.health.ny.gov/system/files/documents/2023/05/all-ages-covid-19-guidance_5.23.2023.pdf, May 23, 2023, 12 pgs.

Preliminary Criteria for the Evaluation of Digital Contact Tracing Tools for COVID-19, CDC Centers for Disease Control and Prevention, Archived Document (COVID-19), downloaded from https://www.google.com/url?sa=t&rct=j&q=&esrc=s&source=web&cd=&cad=rja&uact=8&ved=2ahUKEwj37ar_zY7_AhX_FFkFHdALBNkQFnoECA0QAO&url=https%3A%2F%2Fwww.cdc.gov%2Fcoronavirus%2F2019-ncov%2Fdownloads%2Fphp%2Fprelim-eval-criteria-digital-contact-tracing.pdf&usg=AOvVaw0-zDZ7FU3W3kVBrSsA4p_s , May 3, 2020, 3 pgs.

COVID-19 Contact Tracing Playbook, downloaded from *Introduction—Covid-19 Contact Tracing Playbook* (resolvetosavelives.org), Dec. 21, 2020, 65 pgs.

How Trace Together Works, A Singapore Government Agency Website, Youtube video, downloaded from https://www.tracetogether.gov.sg/, Feb. 9, 2023, 3 pgs.

Digital Solutions for COVID-19 Response, CommCare, downloaded from https://www.dimagi.com/covid-19/ , May 24, 2023, 7 pgs.

WHO First Few X (FFX) COVID-19 Protocol—A CommCare Template App by Dimagi, CommCare Youtube video downloaded from https://www.youtube.com/watch?v=MwVXaQCWat4&list=PLVmwIEfrcKgrn8_ujYNM39mU-i5kuyGZ0n&index=4, May 24, 2023, 4 pgs.

PACT: Private Automated Contact Tracing, Youtube video, downloaded from https://pact.mit.edu/, May 24, 2023, 4 pgs.

Apple and Google, Privacy-Preserving Contact Tracing, downloaded from https://covid19.apple.com/contacttracing May 24, 2023, 1 page.

Jennifer Valentino-Devries, Natasha Singer and Aaron Krolik, A Scramble for Virus Apps That Do No Harm, NY Times, Apr. 29, 2020, downloaded from https://www.google.com/url?sa=t&rct=j&q=&esrc=s&source=web&cd=&cad=rja&uact=8&ved=2ahUKEwl2hpvGy17_AhXNjokEHVTEBhQQFnoECA0QAQ&url=https%3A%2F%2Fwww.nytimes.com%2F2020%2F04%2F29%2Fbusiness%2Fcoronavirus-cellphone-apps-contact-tracing.html&usg=AOvVaw29poCU089D5WzsY_GDcHvT , 5 pgs.

World Health Organization, Ethical considerations to guide the use of digital proximity tracking technologies for COVID-19 contact tracing, Interim Guidance, downloaded from https://www.who.int/publications/i/item/WHO-2019-nCoV-Ethics_Contact_tracing_apps-2020.1, May 28, 2020, 6 pgs.

* cited by examiner

SYSTEMS AND METHODS FOR MULTIDIMENSIONAL ACCESS SYSTEM FOR DISTRIBUTED SITES

FIELD OF THE INVENTION

The invention relates generally systems and methods for managing access to a plurality of sites at a variety of locations which may or may not have heath checks and/or vaccine check requirements. In particular, to systems and methods for remote badging and/or computer access, automatic individual verification, automatic vaccine verification and/or automatically remotely determining an individual's physical presence at a site.

BACKGROUND

Currently many organizations and businesses have multiple locations (e.g., facilities or sites). The sites can be distributed in a state, in a country and/or around the world. Many organizations/businesses include badging systems where employees can swipe into and/or out of facilities. For example, some buildings use a badging system to allow employees to swipe to open a door.

Some companies, depending on location, may have a badging system to allow employees to swipe to allow turnstile type access when a security guard is present, while the same company may have another site in a different location that does not require badging to enter to the location, and employees can simply enter the building once it is open. There can be a variety of employee entry policies (e.g., badge swiping, checking in with a front desk employee, entering, entering and signing a logbook, and/or punching a timecard). Each employee entry policy can be time dependent, for example, a facility may employ checking in with a front desk employee Monday through Friday, 9-5, and signing a logbook outside of those hours.

Typically, entrance and badging systems focus on whether an employee works for the company and thus is allowed entry to the facility. At most, current system may limit the time period an employee can enter the facility, for example, not allowing an employee that works the night shift to enter during the daytime hours.

Upon declaration of the Covid-19 global pandemic, the need to track each and every employee's entrance into facilities, to track whether an employee was infected, exposed, and if so, make sure the employee was staying out of the workplace for the requisite period of time, managing notifications and checks for coming back to the office became important. However, current badging and entry systems are not equipped to make these determinations nor perform this tracking, nor can these determinations be made in a sufficient period to time to have a relevant outcome (e.g., prevent an exposed employee from entering a building).

Additionally, each local health organization can have disparate requirements adding complexity for a global organization. For example, a first country can define a quarantine period as 5 days while a second country can define a quarantine period as 10 days. A first country can have a vaccine card that has a first format and a second country can have a vaccine card that has a second format.

Determining whether each and every employee in a large organization with worldwide offices having a variety of possible entry management protocols that is present at a facility has complied with a variety of sometimes country, sometimes city, sometimes organizational, sometimes team dependent health checks and vaccine requirements in real time before giving access to a facility and/or computing equipment can be a challenging task.

SUMMARY OF THE INVENTION

One advantage of the invention can include an ability to remotely determine whether an individual (e.g., employee, user, person) is physically present at a site for a variety of access environments. Another advantage of the invention can include an ability to perform health checks and/or vaccine checks remotely configured to a particular site's location and/or policies associated with the site in real-time. Another advantage of the invention can include automatic vaccine verification for a wide variety of site locations with varying requirements.

Another advantage of the invention can include restricting access to one or more locations based on vaccination or health status. Another advantage of the invention can include identifying those who have violated policy by entering a location if their vaccination or health status precludes them under local policy.

In one aspect, the invention involves a computerized-method for managing access to a plurality of sites. The computerized-method involves receiving, at a processor, an arrival event, wherein the arrival event includes a swipe event occurring at a badge reader or login event at a computer. The computerized-method also involves determining, by the processor, a location for the arrival event based on one or more data items associated with the arrival event. The computerized-method also involves determining, by the processor, a health policy for the arrival event based on the location, wherein the health policy includes a health screener requirement and a vaccine screener requirement. The computerized-method also involves for an arrival event that fails the health policy or the vaccine screener requirement, preventing, by the processor, access to a computing device associated with the user and presenting a message to a user associated with the arrival event to leave the site associated with the arrival event. The computerized-method also involves for an arrival event that passes the health policy or the vaccine screener policy, outputting, by the processor, to the user associated with the arrival event a passing indicator and allowing the user to access to a computing device associated with the user.

In some embodiments, the health screener requirement and the vaccine screener requirement are configurable. In some embodiments, configurable parameters for the health screener requirement includes completion of a health attestation form, a completion of an online covid test, a temperature check, or any combination thereof.

In some embodiments, configurable parameters for the vaccine screener includes vaccine check needed, number of vaccine doses needed, duration since last vaccine, or any combination therefor.

In some embodiments, the vaccine screener requirement includes verifying the vaccine card of a user associated with the arrival event.

In some embodiments, the computerized-method further comprises receiving, by the processor, from a user an indication that a covid event has occurred, and determining, by the processor, based on a user profile associated with the user, one or more additional users who are close contacts to the user based on logged arrival events for the location.

In another aspect, the invention includes a non-transitory computer program product comprising instructions which, when the program is executed cause a processor to receive an arrival event, wherein the arrival event includes a swipe event occurring at a badge reader or login event at a computer and determine a location for the arrival event based on one or more data items associated with the arrival event. The non-transitory computer program product comprising instructions which, when the program is executed also cause the processor to determine a health policy for the arrival event based on the location, wherein the health policy includes a health screener requirement and a vaccine screener requirement. The non-transitory computer program product comprising instructions which, when the program is executed also cause the processor to for an arrival event that fails the health policy or the vaccine screener requirement, preventing, by the processor, access to a computing device associated with the user and presenting a message to a user associated with the arrival event to leave the site associated with the arrival event. The non-transitory computer program product comprising instructions which, when the program is executed also cause the processor to for an arrival event that passes the health policy or the vaccine screener policy, outputting, by the processor, to the user associated with the arrival event a passing indicator and allowing the user to access to a computing device associated with the user.

In some embodiments, the health screener requirement and the vaccine screener requirement are configurable. In some embodiments, configurable parameters for the health screener requirement includes completion of a health attestation form, a completion of an online covid test, a temperature check, or any combination thereof. In some embodiments, configurable parameters for the vaccine screener includes vaccine check needed, number of vaccine doses needed, duration since last vaccine, or any combination therefor.

In some embodiments, the vaccine screener requirement includes verifying the vaccine card of a user associated with the arrival event. In some embodiments, the non-transitory computer program comprising instructions which, when the program is executed also cause the processor to receive from a user an indication that a covid event has occurred, and determine based on a user profile associated with the user, one or more additional users who are close contacts to the user based on logged arrival events for the location.

In another aspect, the invention involves a computerized-method for automatically determining a person physical presence in a facility. The computerized-method involves receiving, via a server a plurality of login events for each computing device of a plurality of computing devices, wherein each login event of the plurality of login events comprises a location of the computer and a login time. The computerized-method also involves determining, via the server, whether each login event of the plurality of login events is a remote login by: i) checking at least two remote session for the respective login event based on the login time of the respective login event, and ii) if the respective login event is present in both of the at least two remote session ranges then the respective login event is a remote login, otherwise, the respective login event is not a remote login. The computerized-method also involves for all login events that are not remote logins determining, via the server, that a user associated with the computing device of the respective login event is physically present in the facility at the start time of the respective login event, and transmit a notification to a display of the computing device the user, wherein the notification is one of a reminder to participate in a health check, an indicator that the user is being counted as physically present in the facility or any combination thereof.

In some embodiments, checking the at least two remote session ranges also involves analyzing the respective login event for ICA data including source, start time, end time or any combination thereof. In some embodiments, checking the at least two remote session ranges further comprises analyzing the respective login event for RDP data including source, resume time, end time or any combination thereof.

In some embodiments, checking the at least two remote session ranges also involves analyzing the respective login event for AOVPN data including computer powered on, user sessions, or any combination thereof.

In some embodiments, the computerized-method also involves aligning the start time of the two remote session ranges for the login event. In some embodiments, a third remote session login time is determined. In some embodiments, for all logins events of the plurality of login events that are remote logins. In some embodiments, for a login event of the plurality of events that is not a remote login, generating an alert that is an indicator that the user associated with login event is not allowed in the facility.

In another aspect, the invention involves a non-transitory computer program product comprising instructions which, when the program is executed cause a server to receive a plurality of login events for each computing device of a plurality of computing devices, wherein each login event of the plurality of login events comprises a location of the computer and a login time. The non-transitory computer program product comprising instructions which, when the program is executed also cause a server to determine whether each login event of the plurality of login events is a remote login by i) checking at least two remote session for the respective login event based on the login time of the respective login event and ii) if the respective login event is present in both of the at least two remote session ranges then the respective login event is a remote login, otherwise, the respective login event is not a remote login. The non-transitory computer program product comprising instructions which, when the program is executed also cause a server to for all login events that are not remote logins determining, via the server, that a user associated with the computing device of the respective login event is physically present in the facility at the start time of the respective login event. The non-transitory computer program product comprising instructions which, when the program is executed also cause a server to transmit a notification to a display of the computing device the user, wherein the notification is one of a reminder to participate in a health check, an indicator that the user is being counted as physically present in the facility or any combination thereof.

In some embodiments, checking the at least two remote session ranges further involves analyzing the respective login event for ICA data including source, start time, end time or any combination thereof. In some embodiments, checking the at least two remote session ranges further involves analyzing the respective login event for RDP data including source, resume time, end time or any combination thereof.

In some embodiments, checking the at least two remote session ranges further involves analyzing the respective login event for AOVPN data including computer powered on, user sessions, or any combination thereof.

In some embodiments, the non-transitory computer program product further comprises instructions which, when the program is executed also cause a server to align the start time of the two remote session ranges for the login event.

In some embodiments, a third remote session login time is determined. In some embodiments, for all logins events of the plurality of login events that are remote logins. In some embodiments, a login event of the plurality of events that is not a remote login, generating an alert that is an indicator that the user associated with login event is not allowed in the facility.

In another aspect, the invention involves a computerized-method for vaccine verification. The method involves receiving, via processor, a vaccine card in an electronic format and a plurality of data items. The method also involves performing, via the processor, text recognition on the vaccine card. The method also involves determining, via the processor, which recognized text is key text from the vaccine card based on a configuration file, wherein the configuration file is one configuration file of a plurality of configuration files. The method also involves transmitting, via the processor, a vaccine card verified indicator to a display if all of the plurality of data items has at least one match from the recognized key text, otherwise transmitting a vaccine card not verified indicator to the display.

In some embodiments, the plurality of data items are name, date of birth, vaccine manufacturer, vaccine date, or any combination thereof. In some embodiments, performing text recognition on the vaccine card further involves using an OCR tool on the vaccine card. In some embodiments, determining, via the processor, which recognized text is key text from the vaccine card further comprises using one or more machine learning models.

In another aspect, the invention includes a non-transitory computer program product comprising instructions which, when the program is executed cause a processor to receive a vaccine card in an electronic format and a plurality of data items. The non-transitory computer program product further comprises instructions which, when the program is executed causes a processor to perform text recognition on the vaccine card. The non-transitory computer program product further comprises instructions which, when the program is executed causes a processor to determine which recognized text is key text from the vaccine card based on a configuration file, wherein the configuration file is one configuration file of a plurality of configuration files; and transmit a vaccine card verified indicator to a display if all of the plurality of data items has at least one match from the recognized key text, otherwise transmitting a vaccine card not verified indicator to the display.

In some embodiments, the plurality of data items are name, date of birth, vaccine manufacturer, vaccine date, or any combination thereof. In some embodiments, performing text recognition on the vaccine card further comprises using an OCR tool on the vaccine card.

In some embodiments, determining, via the processor, which recognized text is key text from the vaccine card further comprises using one or more machine learning models. In some embodiments, the electronic format is any electronic photo format.

BRIEF DESCRIPTION OF THE DRAWINGS

Non-limiting examples of embodiments of the disclosure are described below with reference to figures attached hereto that are listed following this paragraph. Dimensions of features shown in the figures are chosen for convenience and clarity of presentation and are not necessarily shown to scale.

The subject matter regarded as the invention is particularly pointed out and distinctly claimed in the concluding portion of the specification. The invention, however, both as to organization and method of operation, together with objects, features and advantages thereof, can be understood by reference to the following detailed description when read with the accompanied drawings. Embodiments of the invention are illustrated by way of example and not limitation in the figures of the accompanying drawings, in which like reference numerals indicate corresponding, analogous or similar elements, and in which:

It will be appreciated that for simplicity and clarity of illustration, elements shown in the figures have not necessarily been drawn accurately or to scale. For example, the dimensions of some of the elements can be exaggerated relative to other elements for clarity, or several physical components can be included in one functional block or element.

DETAILED DESCRIPTION

In the following detailed description, numerous specific details are set forth in order to provide a thorough understanding of the invention. However, it will be understood by those skilled in the art that the invention can be practiced without these specific details. In other instances, well-known methods, procedures, and components, modules, units and/ or circuits have not been described in detail so as not to obscure the invention.

In general, methods and systems for managing access to a plurality of sites is provided. Granting access to the plurality of sites can depend on the access type of each particular site (e.g., badging, key entry and/or other access methods), any access requirement (e.g., vaccine requirements and/or health check requirements) and/or historical information collected regarding a user/employee (e.g., whether the employee was covid positive and quarantining period has not yet expired). The methods and systems for managing access can include automatically determining a person's physical presence at a site. For example, in some scenarios an employee can remote login to a desktop computer at a site and then visit the site later in the day. It can be desirable to determine when this person is physically present at the site or remote logged in to a computer at the site. The methods and system can also include automatic vaccine verification. Automatic vaccine verification can be desirable as vaccine requirements can vary between locations such that vaccine verification can be complex as well as voluminous for a large enterprise.

Figure 1:
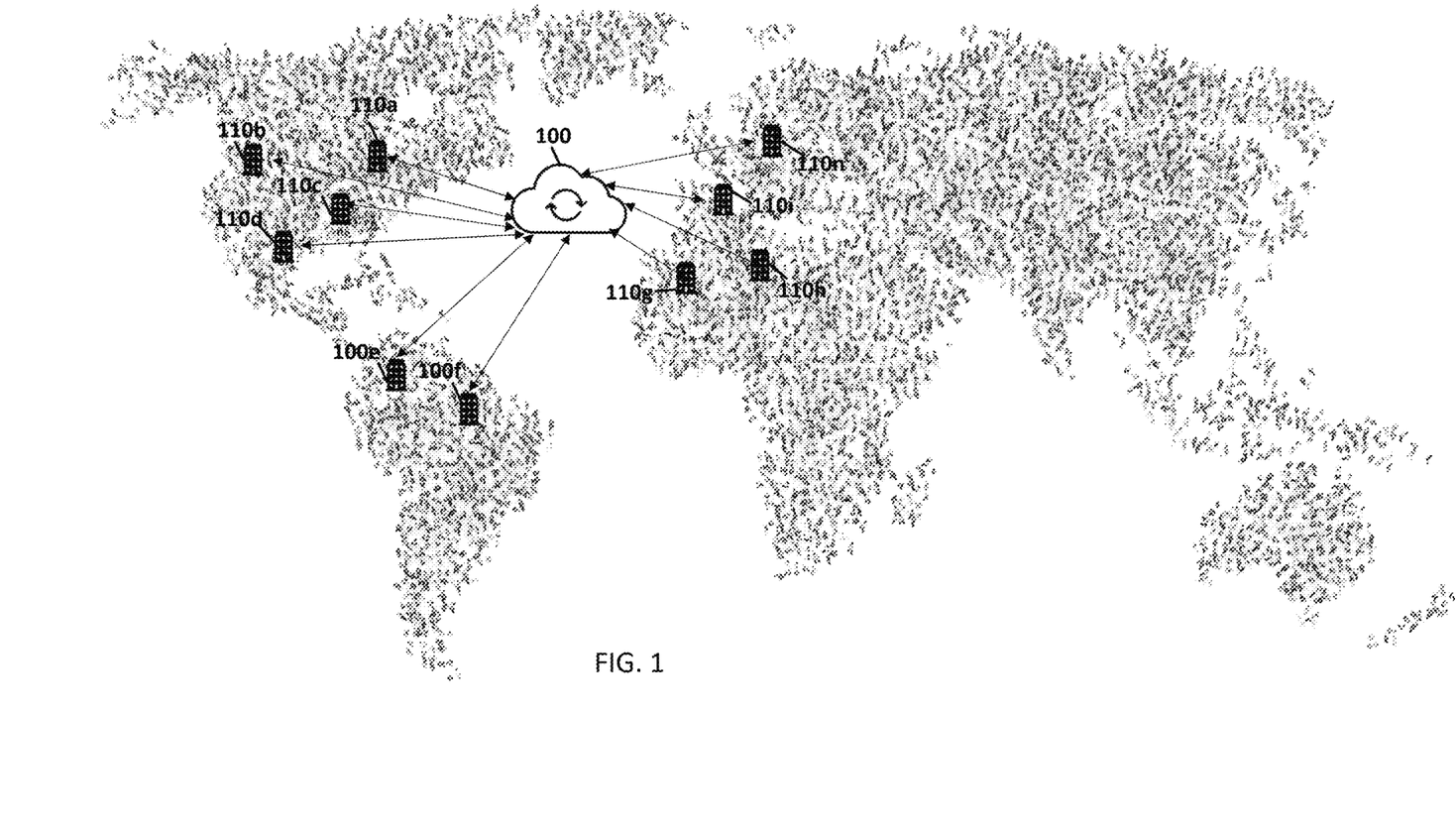
FIG. 1 is a diagram of an example organization having sites at various locations, according to some embodiments of the invention.

FIG. 1 is a diagram of an example organization having sites at various locations, according to some embodiments of the invention. The example organization can have multiple sites 110*a*, 110*b*, 110*c*, 110*d*, 110*e*, 110*f*, 110*g*, 110*h*, 110$i$, ... 110$n$, generally 110, spread across the world, connected via network 100. Each of the multiple sites 110 can include one or more computing devices (e.g., computers and/or other networking elements), to communicate with network 100. Network 100 can be a private network that communicates with the Internet (not shown) to facilitate communication with each of the multiple sites 110. The network 100 can include one or more processors, one or more servers, and/or additional networking elements as is known in the art.

Each site of the multiple sites 110 can allow access to individuals (e.g., employees, contractors, visitors, and/or any other person who may need to access the site), based on local requirements, requirements based on site type (e.g., building with a doorman, building with a swipe key entry, open building), and/or other policies as defined for each particular site.

Allowing access can include allowing physical access into the building, allowing access into one or more rooms or areas within a facility, and/or allowing access to computers.

Figure 1A:
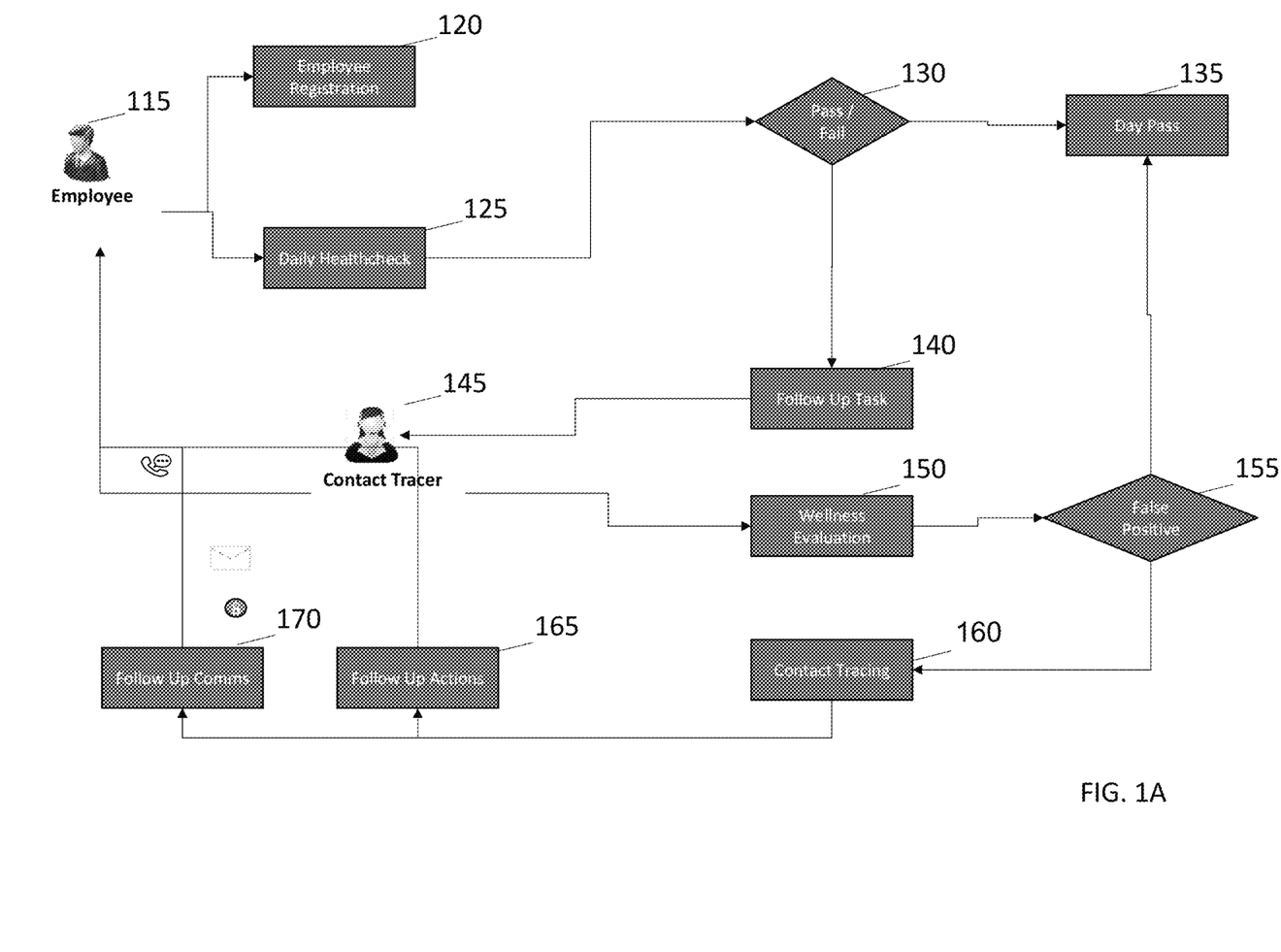
FIG. 1A is a high-level diagram showing flow of a method through a system for managing health checks and/or access for a plurality of sites, according to some embodiments of the invention.

FIG. 1A is a high-level diagram showing flow of a method through a system for managing health checks and/or access for a plurality of sites (e.g., organization with many locations), according to some embodiments of the invention. The system can be implemented via an application on an employees mobile device that is in communication with one more servers.

An employee 115 can register 120 with the system (e.g., via an app on their mobile phone). Once the employee 115 is registered, the employee 115 can subsequently access the system to complete a daily health check 125. The daily health check can be a list of questions the employee 115 must answer regarding their health (e.g., whether or not they have had covid, whether they have a fever, whether they have a sore throat, and/or other questions related to the health of the employee 115). The daily health check questions can be configurable.

The daily health check can be checked for pass or failure 130. If the employee 115 passes the daily health check then the employee 115 can obtain a day pass 135 which can allow them access to their work site for the day (e.g., swipe a badge and show a day pass that can be generated on app). If they fail, then the employee's 115 badge can be disabled and/or computer access can be disabled (e.g., in sites where badging is not enabled).

If the employee 115 fails the daily health check a follow up task 140 is assigned to a contact tracer 145 who can probe the employee 115 to ask for further information. In some embodiments, the contact tracer 145 is another computer that automatically performs the tasks of the contact tracer 145. For example, a chat bot, or a chat bot that GPT enabled.

The task 140 can be based on a location of the employee (e.g., country, state, city, particular office building). In some embodiments, there can be multiple tasks within task 140. In some embodiments, there are a plurality of task templates and the particular task templates of the plurality of task templates that are instantiated are dependent upon the employees location.

When an employee 115 is issued a day pass 135, the employee 115 is granted access to enter computing resources for the day.

The contact tracer 145 can perform a wellness evaluation 150. The wellness evaluation 150 can involve questioning the employee 115 regarding factors that may create a false failure of the daily health check (e.g., a false positive covid test or a false positive flu test). For example, an employee 115 may have an underlying condition that causes elevated temperature such that elevated temperature is not an indicator that the employee 115 is sick. In this manner, the contact tracer 145 can determine a false outcome.

The wellness evaluation can be checked 155 for a false outcome of the daily health check of a fail (e.g., a false positive covid test) or an accurate outcome of the daily health check (e.g., the positive covid test that caused the daily health check to fail was accurate). If it was a false positive, then the employee 115 can obtain a day pass 135. If it was a true positive, then contact tracing 160 can be performed.

The contact tracing 160 can involved identifying who the employee 115 has been in contact with in the configurable number of days (e.g., the configurable number of days can be a local requirement, for example, five previous days), creating follow up actions 165 for each of the employees that the employee 115 has been in contact with, and follow up communications 170. For example, if the employee 155 had lunch with one other employee and a meeting with two other employees, a contact encounter participant table can be created (e.g., at the server) to keep track of who the employee has been in contact with. In this example, the employee 115 has been in contact with three employees.

The follow up actions 165 can involve sanitizing desks, have the employees prove they are healthy to return back to work (e.g., take a covid test), and/or quarantine for a certain number of days. The follow up communication 170 can involve sending an employees manager message that the employee 115 is quarantining for the configured number of days, and at the end of the quarantine again notifying the manager that the employee 115 is done and returning to work.

In some embodiments, if it was a true positive then a life event data item can be created for an employee (e.g., by capturing the data via the mobile app and storing the data in the server for the employee). The life event data item can be a timeline for the employee that keeps track of health related events of the user that were entered into the app. For example, an employee may have had covid in 2020, been hospitalized in 2020, recovered in 2020, had a false covid positive in 2021, but then followed by a true positive later in 2021. In this manner a life event data item for an employee can be created.

In some embodiments, for an employee that truly fails the health pass (e.g., has a covid positive), a case data item is created (e.g., at the server) to maintain all of the data items as described associated with a covid positive in one data repository.

Figure 2:
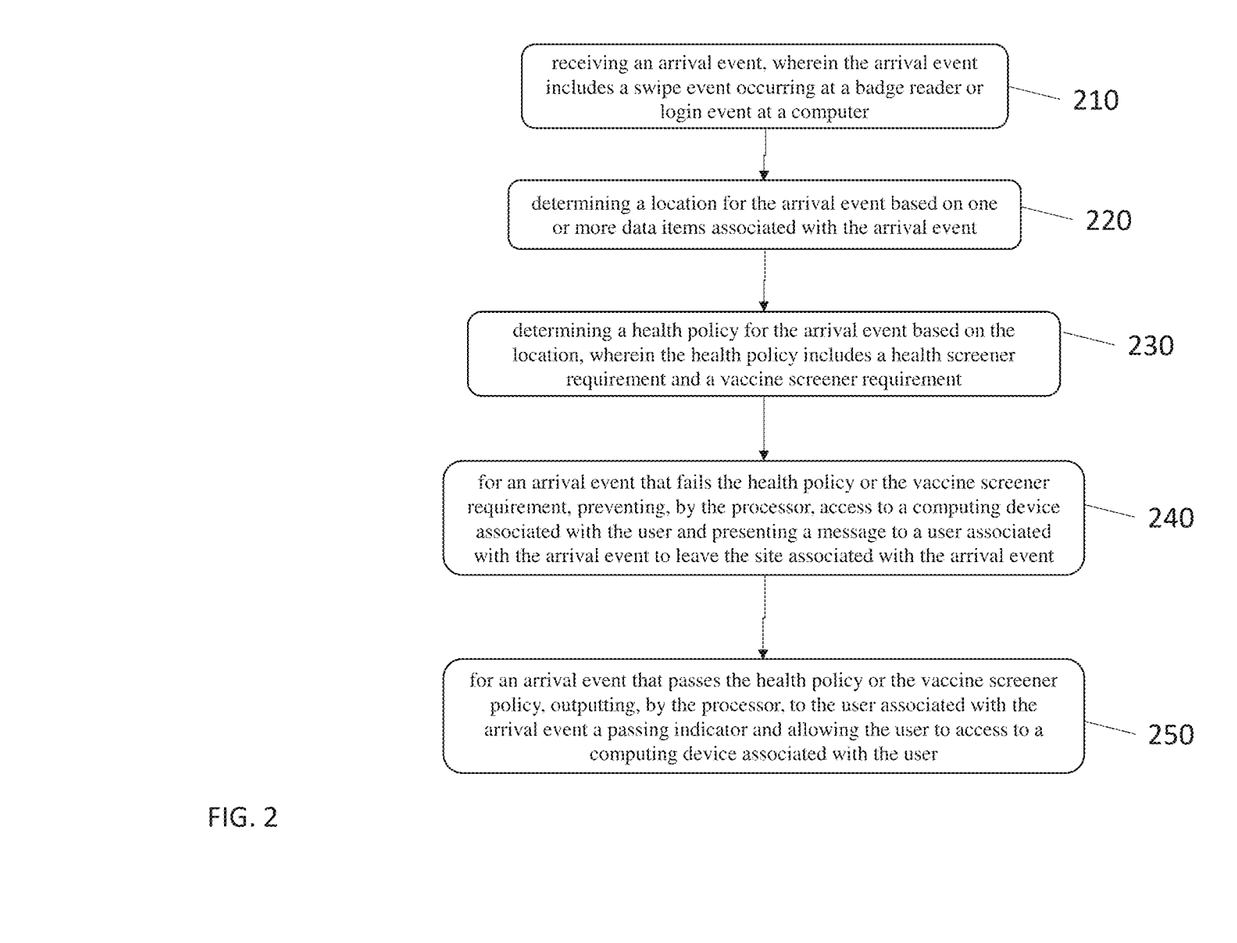
FIG. 2 is a flow chart of a method for managing access to a plurality of sites according to some embodiments of the invention.

FIG. 2 is a flow chart of a method for managing access to a plurality of sites (e.g., sites 110 as described above with respect to FIG. 1) according to some embodiments of the invention.

The method can involve receiving an arrival event (e.g., at a site 110$a$ of a plurality of sites 110 of an organization as shown above with respect to FIG. 1), wherein the arrival event includes a swipe event occurring at a badge reader or login event at a computer (Step 210).

A login event at a computer can be a person logging into the computer with credentials. The credentials can include swiping of a badge for entry to a location, entry of a username and/or password. In some embodiments, if the computer is locked, the arrival event occurs when the computer is unlocked.

The method can involve determining (e.g., by a processor as described above in FIG. 1) a location for the arrival event based on one or more data items associated with the arrival event (Step 220). The one or more data items can be a location associated with the badge reader data and/or location information associated with the location of the computer that the user logged in on or unlocked.

The method can involve determining a health policy for the arrival event based on the location, wherein the health policy includes a health screener requirement and a vaccine screener requirement (Step 230).

The health policy can be based on a configuration file. The configuration file can include a language selection for the health policy and/or a regional covid configuration. The regional covid configuration can include a) vaccine controls, b) vaccine expiration controls, c) case expiration controls, and/or d) non-compliance controls.

The vaccine controls can include:
a. Vaccine exclusion: if enabled, can restrict a location from capturing vaccine data. For example, it can be required to keep employees health information private, and thus the system can be restricted from capturing vaccine data for the arrival event;
b. Badge automation via vaccination: if enabled, can enable/disable employee badges based on vaccination status. For example, for a given organization, one site can require that each arrival event must prove vaccination (e.g., covid-19) whereas for a different site in the same organization the arrival even does not need to prove vaccination;
c. Target pending rejection: if proof of vaccination is deemed to be incomplete or insufficient (e.g., partial vaccination, uploaded proof is unclear or illegible), the vaccination status can be placed in a pending rejection status, giving the employee a configurable period of time to provide updated proof before classifying them as unvaccinated and subjecting them to policies associated with unvaccinated status;
d. Enforce negative testing: if enabled, can require answering a negative testing question as part of a health check. For example, the negative testing question can include attesting to having taken an at home covid test that was negative;
e. Vaccine proof required: if enabled, can require vaccine proof upload, review, or approval for vaccine record entry; and/or
f. Purging proof: if enabled, can auto-purge vaccine proof records after approval.

The vaccination expiration controls can include:
a. Expiration and/or grace periods for vaccination records. For example, each vaccine record can expire after a predetermined period of time. The predetermined period of time can be based on the date the vaccine was received and/or a duration that the vaccine is valid. The predetermined period of time can have a grace period added on such that even upon expiration the employee is given a grace period before the vaccine expires; and/or
b. Optional enforcement of either initial vaccine series complete and/or vaccinations boosters which can be configurable by location and by vaccine type in order to consider employees vaccination for different automation functions (e.g., badge automation and/or non-compliance). For example, if one location a primary vaccine series may be needed whereas in a second location a primary vaccine series and first booster may be needed, whereas in a third location a second booster may be needed.

The case expiration controls can include:
a. For each case event (e.g., contracting covid), a number of days the case event is active until auto-expiring. The number of days the case is active until auto-expiring can be location dependent, for example, based on a particular health agency associated with a location. For example, in the United States, the Center for Disease Control can require an individual to quarantine for five days whereas the Untied Kingdom, the UK health Security Agency can require that an individual to quarantine for three days. The number of days the case is active can depend upon fever, symptoms, positive testing, travel, close contact, and/or persistent contact. In some embodiments, this if 'Office A' requires employees with symptoms to remain out of the office for 5 days after the onset of symptoms, then the expiration date for an Office A employee's 'Symptoms' life event can be a timestamp of 5 days after the defined 'start date' timestamp on the record. In some embodiments, the number of days a case event is active depends upon other associated data. For example, if a fever started prior to symptoms, then the symptom expiration date can be based off of the fever start date (e.g., rather than the symptom start date), allowing the employee to return to work sooner (e.g., as fever is a symptom in and of itself). If isolation periods for exposure are longer than quarantine periods for positive testing, a 'close contact' event may have an earlier expiration date in coordination with the positive testing date.

The non-compliance controls can include:
a. Determines if a health check is required. The health check can be dependent vaccinations status (e.g., vaccination or unvaccinated); and/or
b. Determines if remote testing (e.g., video assisted doctor testing) is available for the region, and/or if it is required for employees (e.g., unvaccinated employees), and a timeframe for testing.

The regional covid configuration can be managed automatically by the system inserting and/or updating of records based on the name fields. For example, a request can be made for curl to insert or update a regional covid configuration record for the example NY-123 office, as shown below in Table 1:

TABLE 1 curl https://MyDomainName.my.salesforce.com/
services/data/v55.0/sobjects/
RTO_Country_Configuration_c/Name/NY-123 -H
"Authorization: Bearer token" -H
"Content-Type: application/json" -d @sample.json -X PATCH In some embodiments, a request is made in JSON to insert or update a regional configuration record for the example NY-123 office, as shown below in Table 2:

TABLE 2

{
　"Name" : "NY-123",
　"Alt_Name__c" : "New York 123 Office",
　　"Type__c" : "Office",
　"Country__c" :
　{
　　"Name" : 123
　},
　"Badge_Automation_via_Vaccination_c" : "true",
　ETC.....
}

Automated regional covid configuration can reduce errors that can occur during manual management of configuration data.

In some embodiments, there is validation. The validation can include validation of one or more fields. For example, validation of name, alternative name, type, and/or country.

In some embodiments, if no regional covid configuration is available for a particular employee, a default regional covid configuration can be used.

In some embodiments, determining a health policy for the arrival event can involve a web application. The web application can be accessible by individuals (e.g., employees). The web application can include one or more of the following functions which can capture information from a user via a gui and/or other user interfaces as are known in the art:

Registration: users (e.g., employees) can register to use the web application. The user can register with a username and password. A time zone can be captured from the computer and/or entered by the user. The user can also optionally add multiple email address (e.g., up to three) to receive any notifications from the system.

Daily health check: users can enter their current health status (e.g., on a daily basis). The current health status that can be entered can be based on the configuration file as described above. The current health status questionnaire can include questions about current temperature, symptoms, travel, close contacts, Covid positive tests, and/or negative testing. The answers (e.g., data) entered can be stored in the system (e.g., in a database) as a health certification record associated with the particular user. If data is flagged as a failed attestation, a covid case can be auto-generated for the employee with the associated events attached. In some embodiments, the web application can be available only to employees without open covid cases such that if an employee with an open covid case attempts to log into the web application, the login can fail.

Assisted virtual testing: users in certain locations can follow an integrated flow with assisted virtual testing (e.g., Navica/eMed) in order to, for example, run proctored testing for covid. Once testing is complete, the user can be routed back to web application, and the test record can be stored in the system. If positive, a covid case can be auto-generated for the employee.

Profile Management:
Allows an employee to change their selected timezone, language (for HealthCheck display), and external emails. The user can also resend their email for external HealthCheck access Contact Us: Provides regional email/phone details for Covid-associated communications In some embodiments, the daily heath check can involve presenting a user with a self-attestation form. The field presented in the self-attestation form can depend on the regional configuration and/or employee vaccination status, and can include one or more of the following:

1. Fever
   a. If answered 'Yes', the employee can be prompted to enter a fever start date;
2. Symptoms
   a. If answered 'Yes', the employee can be prompted to enter a symptom start date;
3. Close Contact with somebody having Covid
   a. If answered 'Yes', the employee can be prompted to enter a date of the close contact;
4. Travel to location requiring quarantine per local orders
   a. If answered 'Yes', the employee can be prompted to enter most recent date and the location;
5. Covid Positive test
   a. If answered 'Yes', the employee can be prompted to enter the testing Date and test Result Date; and
6. Negative Testing—this question may only be displayed if one or more of the following is true:
   a. The employee's associated regional Country Configuration has 'Enforce Negative Testing' enabled;
   b. The employee is not vaccinated; and/or
   c. The employee has not had a positive covid test in the past 90 days.

Each time a user enters daily health check data, the data can be captured in a new record or a record associated with the user and saved in a database. In some embodiments, based on the answers to the daily health check, a health status can be determined and/or stored on the record. The health pass can be determined as followed:

1. Pass
   a. If questions 1-5 above are answered 'No'
   b. If question 6 is asked, it is answered 'Yes'
2. Fail
   a. Any of questions 1-5 are answered 'Yes'
3. Not Passed
   a. Questions 1-5 are answered 'No'
   b. Question 6 is asked, and it is answered 'No'

The vaccine screener can involve a self-service tool that can automatically screen for vaccine compliance. The vaccine screener tool can present to a user a homepage that presents an employee's existing vaccine records for view. An employee's vaccine records can be uploaded and approved, or uploaded and not yet approved. In some embodiments, an employee has the ability to enter a single initial series vaccination, followed by any number of booster/additional vaccinations. In some embodiments, there can be one or more validations: check that the vaccine record includes a manufacturer and administration date. If the vaccine is a two vaccine series, then the validation can involve checking for two successive dates that are not the same; and/or if the current vaccination seeking approval is a booster, boosters cannot have an earlier shot date than the Initial Series final shot date.

If the employee's associated regional country configuration has 'Vaccine Proof Required' enabled, then vaccination data entry can be submitted with an attachment. Receipt of the attachment can trigger an automated vaccination proof review process. The automated vaccination proof review process can involve:

The vaccination dose can be entered and associated to the employee. The approval setting can be set to 'Pending';
The vaccine proof records (e.g., the attachment) can be inserted and/or associated to the employee.
  The vaccination life event can be associated to this record via the vaccine proof lookup field (e.g., multiple life events can be associated to the same vaccine proof record); and/or
  The attachment file(s) can be linked to the Vaccine Proof object.

A new task can be created for vaccination review. The new task can be associated to the employee and vaccine proof record, and/or assigned to a vaccination proof review queue. For example, if a location is configured to verify proof of vaccination, then a vaccination proof review queue can be created in order to place the vaccine proof record until it can be verified. Task closure can result in any of the following statuses, which can update associated vaccine review fields on the vaccine proof and associated life events:
Approved:
    Approval Status=Approved
    Approver=user closing task
    Review date=date of task closure
Immediate Rejection:
    Approval Status=Rejected
    Approver=user closing task
    Review date=date of task closure
    Rejection Reason=rejection reason provided by user on task closure
    Rejection Comments=comments provided by user on task closure
    Immediate rejection can result immediately auto-cancel associated Vaccination life events
Delayed Rejection:
    Approval Status=Pending Rejection
    Approver=user closing task
    Review date=date of task closure
    Rejection Reason=rejection reason provided by user on task closure
    Rejection Comments=comments provided by user on task closure
    Target Rejection DateTime=Current timestamp+ 'Target Pending Rejection' days count (as found on employee's associated regional Country Configuration)
    Delayed rejection can have a delayed auto-cancel associated Vaccination life events. This cancellation will happen once the 'Target Rejection Datetime' is met. Also, any newly inserted Vaccination records for the employee will auto-cancel records in a Pending Rejection status The employees vaccine records can be automatically recognized, as described in further detail below with respect to FIG. 4.

In some embodiments, the system can transmit automated emails. The automated emails can be transmitted for one or more of the following events:
a. Registration with the system;
b. Newly hired employee;
c. New covid case;
d. Closed covid case;
e. Complex emails for local cases;
f. Contact tracing notification/follow up;
g. Vaccination proof (e.g., submission, rejection, delayed rejection, cancellation, and/or reminder); and/or
h. Non-compliance notifications (e.g., open case, no health check, and/or no negative testing).

Automated emails can be in a multiple language (e.g., English, Spanish, French, and/or Japanese). The automated emails can be templates. The templates can be default templates and/or generated by a particular organization, or location specific for within an organization. Available fields within the template can be based on location and/or policy.

The method can involve for an arrival event that fails the health policy or the vaccine screener requirement, preventing, by the processor, access to a computing device associated with the user and presenting a message to a user associated with the arrival event to leave the site associated with the arrival event (Step 240).

The method can involve for an arrival event that passes the health policy or the vaccine screener policy, outputting, by the processor, to the user associated with the arrival event a passing indicator and allowing the user to access to a computing device associated with the user (Step 250).

In some embodiments, tasks can be automatically generated. Tasks that are auto-generated can be specified via process flows. For example, one or more tasks can be contact tracing follow up tasks, for example, auto-generated when an employee is flagged via the contact-tracing process. The one or more tasks can be vaccine proof review tasks, for example, auto-generated when an employee submits proof for review. The one or more tasks can be call facility deep clean tasks: auto-generated if a covid-positive employee was in the office recently. The one or more tasks can be failed attestation follow up tasks, for example, auto-generated if an employee fails health check.

Figure 3:
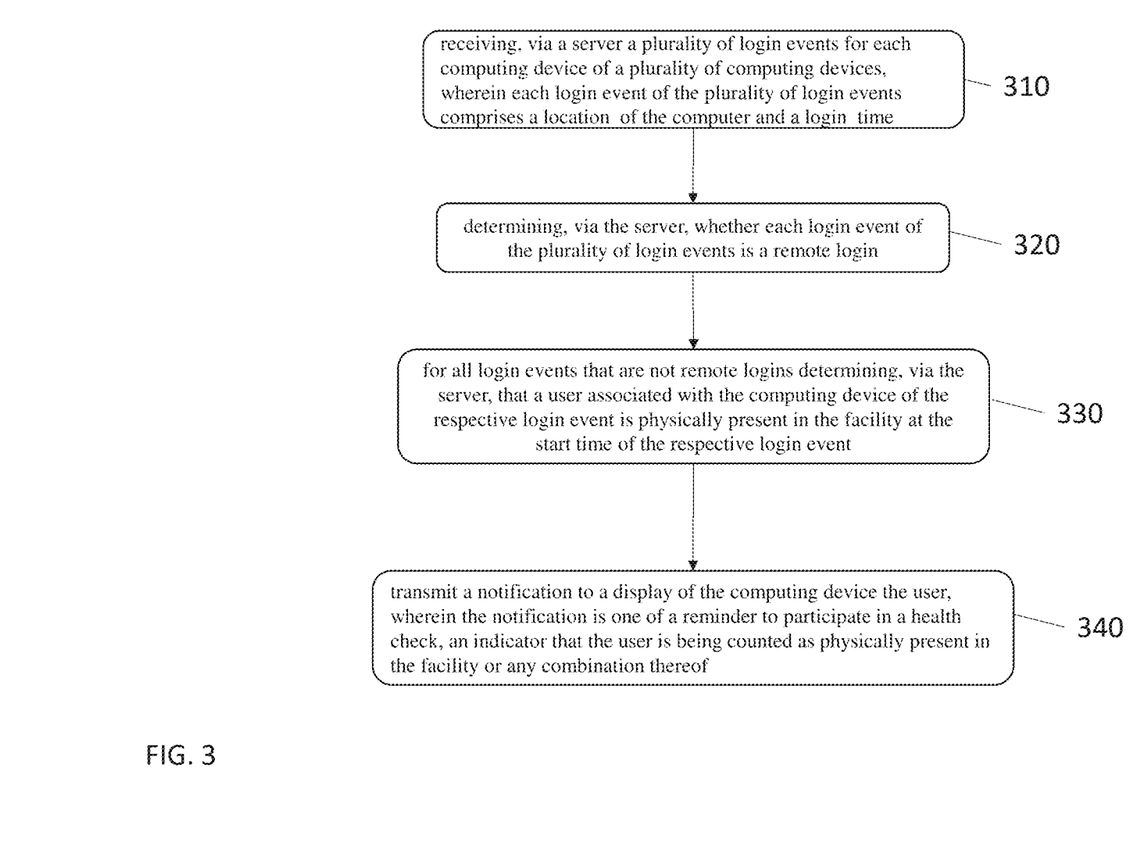
FIG. 3 is a flow chart of a method for automatically determining a person's physical presence in a facility, according to some embodiments of the invention.

FIG. 3 is a flow chart of a method for automatically determining a person's physical presence in a facility, according to some embodiments of the invention.

As described above, it can be desirable to automatically determine a person's physical presence in a facility. For example, an employee may initiate a remote session on a first computing device (e.g., a laptop computer) in a first location (e.g., user's home, hotel, and/or another office) which can connect the employee to a second computing device (e.g., a desktop computer) in an office. The employee can be authenticated when accessing the second computing device. The employee can lock and unlock the second computing device via the first computing device. The employee can log out of the second computing device via the first computing device, close the remote session and/or lock the first computing device, travel to the location of the second computing device, and log into second computing device. In each of these scenarios, it can be desirable to determine the physical location of the employee.

The method can involve receiving, via a server a plurality of login events for each computing device of a plurality of computing devices, wherein each login event of the plurality of login events comprises a login time (Step 310). In some embodiments, each login event includes a location. The login time can be an initial login time (e.g., the first time the employee logged in) or an unlock time (e.g., the time the employee unlocked a locked computer that was in session already). In some embodiments, the login time can be login after an unexpected interruption that caused the user to be unintentionally interrupted from a prior session (e.g., due to an internet interruption). In some embodiments, credentials can be required to be re-entered after a computer has been locked for longer than a predetermined duration (e.g., ten minutes).

In some embodiments, each computing device of the plurality of computing devices is used by one employee at a time, meaning only one employee can be logged into a particular computer at a time.

The method can involve determining, via the server, whether each login event of the plurality of login events is a remote login (Step 320).

In some embodiments, determining whether each login event of the plurality of login events is a remote login can involve checking at least two remote sessions for the respective login event based on the login time of the respective login event. The at least two remote sessions can be different remote session methods for the same login event. The at least two remote sessions for the same login event can be compared to confirm the remote login. For example, for a given login event having at least two remote sessions, the login time (e.g., start time) of each of the remote sessions can be compared and if they are within a threshold (e.g., a second), then the login event can be determined as valid. In some embodiments, the start time and the end time of the two or more remote sessions can be compared. In these embodiments, if there are sessions without a clear end, and another session started, missing data points can be reconciled and whether or not the session is remote determined, even if there are two or more sessions appearing at the same time. In various embodiments, the number of remote sessions that are compared is the number of remote sessions available for the login event.

In various embodiments, remote sessions can be initiated via Citrix ICA ("ICA"), Microsoft Remote Desktop Protocol ("Remote Desktop Connection" and/or "RDP"), and/or Always-On VPN ("AOVPN") (e.g., laptops used out of the office). The remote sessions can include data that shows the computer is being connected to from somewhere other than its physical keyboard/display device. ICA and RDP can be initiated over an internal network. Always-On VPN can be done from external network.

In some embodiments, the data can be collected from the plurality of computing devices depending upon when the plurality of computing devices typically reboot. For example, in a system that typically reboots over Saturday night/Sunday morning, the data collection can be from Sunday after reboot until Saturday at the start of reboot.

In some embodiments, there is a filter that includes criteria for finding data. The filter can include:
  Source—Windows System Event Log, Source Name "TdIca"
  Event Code 1004 or 1006 for Start
  Event Code 1007 for End
  Ignore data center (VMVP* or *WMSHT*) computers
  Group events by computer name and the "IPConnect" value The type of event (e.g. ICA) data can be found in the data (e.g., an event collection system) using the following code as shown below in Table 3:

TABLE 3 splunk_server_group=fed-na index="windesktop_log"
 (EventCode=1007 OR EventCode=1004 OR EventCode=1006)
source="WinEventLog:System" SourceName="TdIca"
host!="VMVP* " AND
host!="*WMSHT*" | rex field-Message " (?< IPConnect>[0-9.:+]+)" |
stats earliest(_time) AS _EarliestTime latest(_time) AS
_LatestTime earliest(EventCode) AS EventCodeE latest(EventCode)
AS EventCodeL by host IPConnect | eval
Closed=if(EventCodeE=EventCodeL, "NO", "YES") | eval
EarliestTime=strftime(_EarliestTime, "%m/%d/%Y %H:%M:%S") | eval
LatestTime=strftime(_LatestTime, "%m/%d/%Y %H:%M:%S") | rename
host as Computer | table Computer EventCodeE EventCodeL
EarliestTime LatestTime Closed In another example, for RDP relevant data collected can be as follows:
  Source—Windows Security Event Log
  Event Code 4778 for Resume (we don't get start of a new RDP session here, we can handle
  that by ignoring that (4624, type 11) in the Hello events, see that later in this doc.
  Event Code 4779 for End
  Ignore data center (VMVP* or *WMSHT*) computers
  Ignore Client_Address="Local" (which shows "fast user switching)
  Group events by computer name and the "IPConnect" value The type of event (e.g. RDP) data can be found in the data (e.g., an event collection system) using the following code as shown below in Table 4:

TABLE 4 index="windesktop_log" splunk_server_group=fed-na
 (EventCode=4778 OR EventCode=4779) source="WinEventLog:Security"
Client_Address!="LOCAL" host!="VMVP*" AND host!="*WMSHT*" |
mvexpand EventCode | search EventCode!="EventCode" | stats
earliest(_time) AS _EarliestTime latest(_time) AS _LatestTime
earliest(EventCode) AS EventCodeE latest(EventCode) AS
EventCodeL by host Client_Address Session_Name | eval
Closed=if(EventCodeE=EventCodeL, "NO", "YES") | eval
EarliestTime=strftime(_EarliestTime, "%m/%d/%Y %H:%M:%S") | eval
LatestTime=strftime(_LatestTime, "%m/%d/%Y %H:%M:%S") | rename
host as Computer | table Computer EventCodeE EventCodeL
EarliestTime LatestTime Closed In another example, for AOVPN relevant data can be uploaded approximately every thirty minutes collected can be as follows:
  Machine sessions only
  Due to the file-based nature of the source, this is fixed to "past seven (7) days"—does not use the earliest/latest values we give it in the Splunk command The type of event (e.g. AOVPN) data can be found in the data (e.g., an event collection system) using the following code as shown below in Table 4:

TABLE 5

| inputlookup aovpn_sessions.csv | search TunnelType="Machine" |
eval LatestTime = if(isnull(EndTime), StartTime, EndTime) |
where strptime(LatestTime, "%m/%d/%Y %I:%M %P
%Z")>=relative_time(now( ), "-7d") AND strptime(LatestTime,
"%m/%d/%Y %I:%M %P %Z")<=relative_time(now( ), "-1s") | eval
SortTime = strptime(LatestTime, "%m/%d/%Y %I:%M %P") |
rename
ClientName as Computer | table Computer StartTime EndTime
DurationMinutes SortTime In some embodiments, determining whether each login even of the plurality of login events can involve if the respective login event is present in both of the at least two remote session ranges then the respective login evet is a remote login, otherwise, the respective login event is not a remote login.

In various embodiments, a user can access a computer for the first time, unlock after returning from a break, or start another day. In some embodiments, the events tracked within the computer when the session is not remote can include: within windows Security Event Log: Event Codes 4624 with Logon_Type 2, 10 or 11 and Logon_Process User32, Event Code 4778 and/or Event Code 4801 and/or Ignore data center (VMVP* or *WMSHT*) computers. In some embodiments, language packs on the computers can affect the collection of events. The event search can accommodate English, French, Japanese.

Each event can be compared against the remote sessions for the event. If there is no remote sessions for the event, then the event is not a remote login. In some embodiments, the one or more remote sessions can have their times modified to, for example synchronize timing between the event and the one or more remote sessions. For example, for events 1004, 1006, and remote session ICA, earliest time can be compared and rounded down to the minute by removing seconds value. For event 1007 and remote session ICA, the latest time can be compared and rounded up by changing seconds to :59. In another example, for event 4778 and remote session RDP, use earliest time can be compared and rounded down to the minute by removing seconds value. For event 4779 and remote session RDP, latest time can be compared and round up by changing seconds to :59. In another example, for AOVPN remote sessions, session times are not rounded.

The method can involve for all login events that are not remote logins determining, via the server, that a user associated with the computing device of the respective login event is physically present in the facility at the start time of the respective login event (Step 330).

The method can involve transmit a notification to a display of the computing device the user, wherein the notification is one of a reminder to participate in a health check, an indicator that the user is being counted as physically present in the facility or any combination thereof (Step 340).

Figure 4:
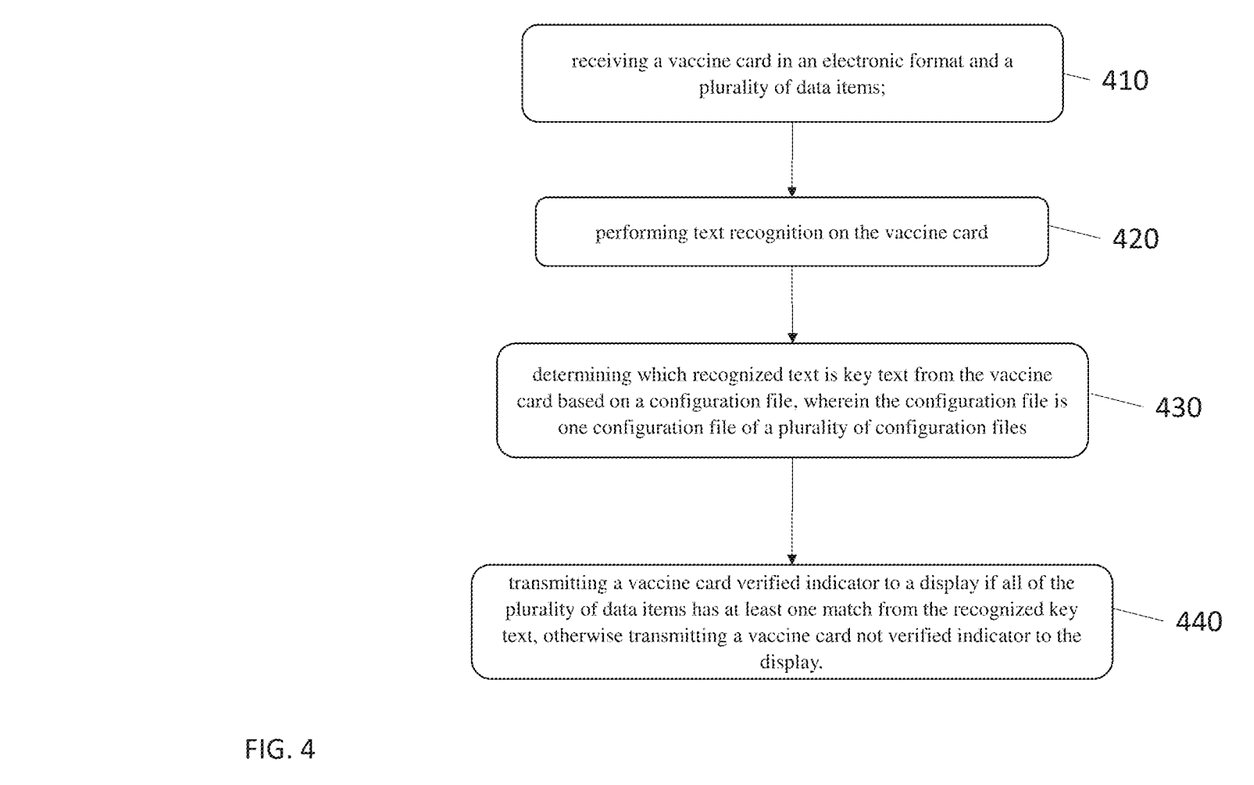
FIG. 4 is a flow chart of a method for vaccine verification, according to some embodiments of the invention

FIG. 4 is a flow chart of a method for vaccine verification, according to some embodiments of the invention.

The method can involve receiving, via processor, a vaccine card in an electronic format and a plurality of data items (Step 410). The plurality of data items can be name, date of birth, vaccine manufacturer, vaccine date, or any combination thereof. The plurality of data items can be vaccine card type dependent. The plurality of data items can be country of origin of for the vaccine card dependent. In some embodiments, an employee can provide their vaccine card via an application on their mobile device.

The method can involve performing, via the processor, text recognition on the vaccine card (Step 420). The text recognition can be performed via OCR.

The method can involve determining, via the processor, which recognized text is key text from the vaccine card based on a configuration file, wherein the configuration file is one configuration file of a plurality of configuration files (Step 430). The configuration file can depend upon location and/or vaccine card type. For example, the United States can have a vaccine card that is different in form than the UK. The way a vaccine card is filled in can be based on region.

In some embodiments, determining which recognized text is key text from the vaccine card further comprises using one or more machine learning models. In some embodiments, OCR data is used to train the models. The models can be location specific, for example, vaccination cards can vary across the globe. For example, a vaccine card in the United States can be very different in format and information from a vaccine card from India. In some embodiments, a vaccine card can vary within a particular country or region, for example, based on vaccine type. There can be one model for each vaccine card type. There can be a configuration of which model to leverage based on location and/or vaccine type.

The method can involve transmitting, via the processor, a vaccine card verified indicator to a display if all of the plurality of data items has at least one match from the recognized key text, otherwise transmitting a vaccine card not verified indicator to the display (Step 440).

For example, once the key text from the vaccine card is extracted, the key text can be compared to employee profiles to determine if the vaccine card can be verified. In some embodiments, the data on the vaccine card may not match the employee profile data perfectly but still be the vaccine card for the employee. For example, if an employees name is Michael Peasy, it may be hand written on a vaccine card as Mike Peasy. In some embodiments, a fuzzy match algorithm is implemented.

In some embodiments, the OCR engine extracts vaccine data (e.g., data that is selected by a user, or automatically determined as relevant). The data that can be extract can include name, data of birth, vaccine manufacturer and/or vaccine date. In some embodiments, the data that is extracted is input by a user.

The extracted data can be compared against an employee record and/or against an employees stored vaccine details. The employees stored vaccine details can be details that were entered via an application by the employee. In some embodiments, the employee's vaccine is verified if the date of birth and the vaccine date are exact matched and the name and vaccine manufacturer is fuzzy matched.

Vaccination status can be captured on each individual. Vaccine effectiveness timeframes may vary from location to location, as well as by primary series and/or booster. Expiration logic was implemented in order to respect location-based timeframes for vaccine effectiveness, and contributes to vaccine status data captured on each employee record.

Figure 5:
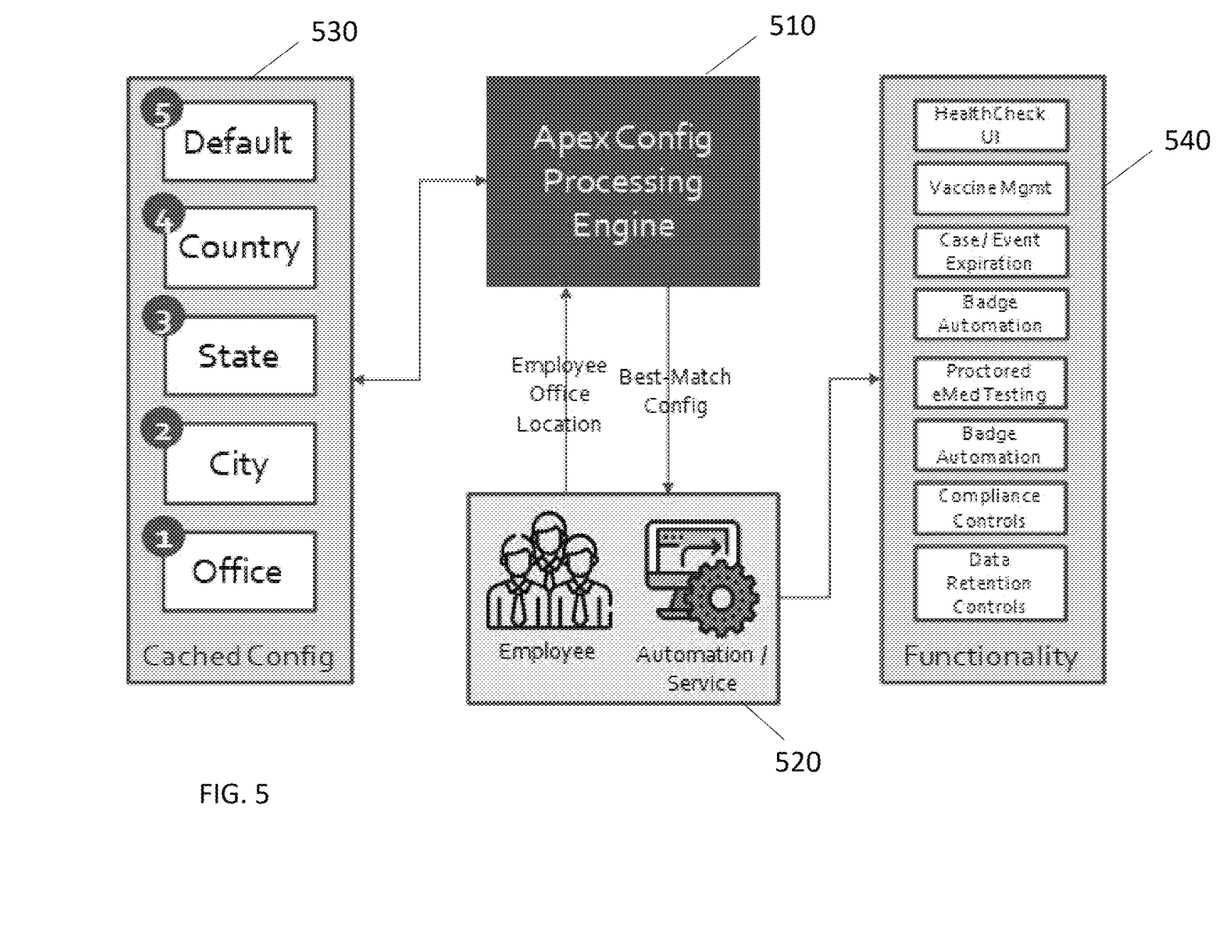
FIG. 5 shows an example of a system architecture for a system for managing access to a plurality of sites, according to some embodiments of the invention.

The following fields can be captured on employee records in order to, for example, consolidate and/or present vaccination status: Vaccine Status: Primary Series Complete: Next Vax Eligibility Date: Vax Expiration Date:

FIG. 5 shows an example of a system 500 architecture for a system for managing access to a plurality of sites, according to some embodiments of the invention.

The system architecture includes a processor 510, one or more employee sites 520, a database including regional covid configuration 530, and/or a server including one more functions 540.

The processor 510 can be on a single computing device or distributed computing devices. The processor 510 can be in communication with the one or more employee sites 520, the database 530, and/or the server 540.

The one or more employee sites 520 can receive a login event from a user (e.g., employee). The login event can be the user physically present at the site or a remote login. The login event can be transmitted to the processor 510. The processor 510 can lookup a region covid configuration 530 associated with the employee in the database 530. The regional covid configuration 530 can be based on the office location, the city, the state, the country and/or a default configuration can be used. Based on the regional covid configuration and/or the employee one or more functions can be called from the server 540. The functions can include any of the functions as described above. For example, health check, vaccine check, case event and/or management, detection of an individual at a facility, automatically verifying a vaccine card or any combination thereof.

Figure 6:
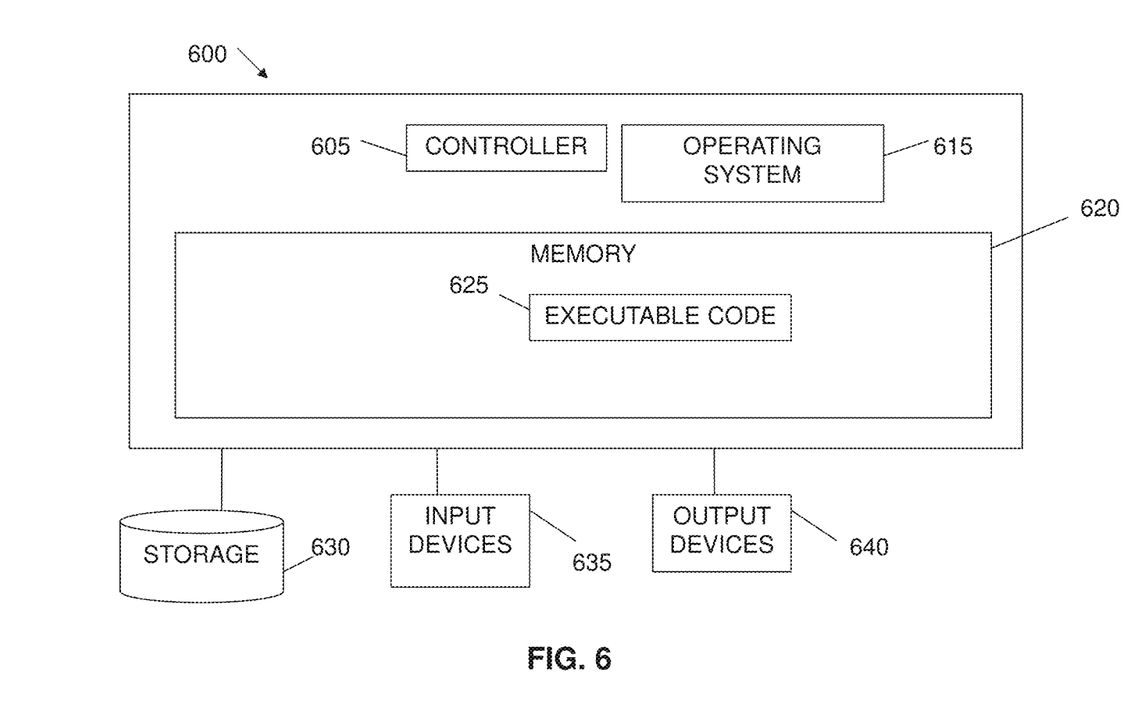
FIG. 6 is a block diagram of a computing device which can be used with embodiments of the invention.

FIG. 6 shows a block diagram of a computing device 600 which can be used with embodiments of the invention. Computing device 600 can include a controller or processor 605 that can be or include, for example, one or more central processing unit processor(s) (CPU), one or more Graphics Processing Unit(s) (GPU or GPGPU), a chip or any suitable computing or computational device, an operating system 615, a memory 620, a storage 630, input devices 635 and output devices 640.

Operating system 615 can be or can include any code segment designed and/or configured to perform tasks involving coordination, scheduling, arbitration, supervising, controlling or otherwise managing operation of computing device 600, for example, scheduling execution of programs. Memory 620 can be or can include, for example, a Random Access Memory (RAM), a read only memory (ROM), a Dynamic RAM (DRAM), a Synchronous DRAM (SD-RAM), a double data rate (DDR) memory chip, a Flash memory, a volatile memory, a non-volatile memory, a cache memory, a buffer, a short term memory unit, a long term memory unit, or other suitable memory units or storage units. Memory 620 can be or can include a plurality of, possibly different memory units. Memory 620 can store for example, instructions to carry out a method (e.g. code 625), and/or data such as user responses, interruptions, etc.

Executable code 625 can be any executable code, e.g., an application, a program, a process, task or script. Executable code 625 can be executed by controller 605 possibly under control of operating system 615. For example, executable code 625 can when executed cause masking of personally identifiable information (PII), according to embodiments of the invention. In some embodiments, more than one computing device 600 or components of device 600 can be used for multiple functions described herein. For the various modules and functions described herein, one or more computing devices 600 or components of computing device 600 can be used. Devices that include components similar or different to those included in computing device 600 can be used, and can be connected to a network and used as a system. One or more processor(s) 605 can be configured to carry out embodiments of the invention by for example executing software or code. Storage 630 can be or can include, for example, a hard disk drive, a floppy disk drive, a Compact Disk (CD) drive, a CD-Recordable (CD-R) drive, a universal serial bus (USB) device or other suitable removable and/or fixed storage unit. Data such as instructions, code, NN model data, parameters, etc. can be stored in a storage 630 and can be loaded from storage 630 into a memory 620 where it can be processed by controller 605. In some embodiments, some of the components shown in FIG. 6 can be omitted.

Input devices 635 can be or can include for example a mouse, a keyboard, a touch screen or pad or any suitable input device. It will be recognized that any suitable number of input devices can be operatively connected to computing device 600 as shown by block 635. Output devices 640 can include one or more displays, speakers and/or any other suitable output devices. It will be recognized that any suitable number of output devices can be operatively connected to computing device 600 as shown by block 640. Any applicable input/output (I/O) devices can be connected to computing device 600, for example, a wired or wireless network interface card (NIC), a modem, printer or facsimile machine, a universal serial bus (USB) device or external hard drive can be included in input devices 635 and/or output devices 640.

Embodiments of the invention can include one or more article(s) (e.g. memory 620 or storage 630) such as a computer or processor non-transitory readable medium, or a computer or processor non-transitory storage medium, such as for example a memory, a disk drive, or a USB flash memory, encoding, including or storing instructions, e.g., computer-executable instructions, which, when executed by a processor, server or controller, carry out methods disclosed herein.

One skilled in the art will realize the invention can be embodied in other specific forms without departing from the spirit or essential characteristics thereof. The foregoing embodiments are therefore to be considered in all respects illustrative rather than limiting of the invention described herein. Scope of the invention is thus indicated by the appended claims, rather than by the foregoing description, and all changes that come within the meaning and range of equivalency of the claims are therefore intended to be embraced therein.

In the foregoing detailed description, numerous specific details are set forth in order to provide an understanding of the invention. However, it will be understood by those skilled in the art that the invention can be practiced without these specific details. In other instances, well-known methods, procedures, and components, modules, units and/or circuits have not been described in detail so as not to obscure the invention. Some features or elements described with respect to one embodiment can be combined with features or elements described with respect to other embodiments.

Although embodiments of the invention are not limited in this regard, discussions utilizing terms such as, for example, "processing," "computing," "calculating," "determining," "establishing", "analyzing", "checking", or the like, can refer to operation(s) and/or process(es) of a computer, a computing platform, a computing system, or other electronic computing device, that manipulates and/or transforms data represented as physical (e.g., electronic) quantities within the computer's registers and/or memories into other data similarly represented as physical quantities within the computer's registers and/or memories or other information non-transitory storage medium that can store instructions to perform operations and/or processes.

Although embodiments of the invention are not limited in this regard, the terms "plurality" and "a plurality" as used herein can include, for example, "multiple" or "two or more". The terms "plurality" or "a plurality" can be used throughout the specification to describe two or more components, devices, elements, units, parameters, or the like. The term set when used herein can include one or more items. Unless explicitly stated, the method embodiments described herein are not constrained to a particular order or sequence. Additionally, some of the described method embodiments or elements thereof can occur or be performed simultaneously, at the same point in time, or concurrently.

What is claimed is:

1. A computerized-method for managing access to a plurality of sites, the method comprising:

receiving, at a processor, an arrival event, wherein the arrival event includes a login event at a computer;

determining, by the processor, a location for the arrival event based on one or more data items associated with the arrival event, wherein the one or more data items include location information, wherein determining the location further comprises verifying that the login event is not a remote login by:

checking at least two remote sessions for the login event based on the login time of the login event, the login event not being present in both of the at least two remote session ranges then the respective login event is not a remote login;

determining, by the processor, that a user associated with the computing device of the respective login event is physically present in the facility at the start time of the respective login event; and transmitting, by the processor, a notification to a display of the computing device of the user, wherein the notification is one of a reminder to participate in a health check, an indicator that the user is being counted as physically present in the facility, or any combination thereof;

determining, by the processor, a health policy for the arrival event based on the location and a configuration file, wherein the health policy includes a health screener requirement and a vaccine screener requirement and wherein the configuration file comprises one or more vaccine controls, one or more vaccine expiration controls, one or more case expiration control, or any combination thereof, wherein the one or more vaccine controls comprise restricting collection of vaccine data, placing an incomplete proof of vaccination in a pending state, requiring answering of a negative test questions, require proof of vaccine to be uploaded, automatic removal of vaccine records once approved or any combination, wherein the one or more vaccine expiration controls comprise vaccine expiration period, grace period after vaccine expires to update the vaccine proof, or any combination thereof, wherein one or more case expiration controls comprise a number of days a case is active until automatically expiring, for an arrival event that fails the health policy or the vaccine screener requirement, remotely preventing in real-time, by the processor, access to a computing device associated with the user and presenting a message to a user associated with the arrival event to leave the site associated with the arrival event; and for an arrival event that passes the health policy or the vaccine screener policy, remotely outputting in real-time, by the processor, to the user associated with the arrival event a passing indicator and allowing the user to access to a computing device associated with the user.

2. The computerized-method of claim 1 wherein the health screener requirement and the vaccine screener requirement are configurable.

3. The computerized-method of claim 2 wherein configurable parameters for the health screener requirement includes completion of a health attestation form, a completion of an online covid test, a temperature check, or any combination thereof.

4. The computerized-method of claim 2 wherein configurable parameters for the vaccine screener includes vaccine check needed, number of vaccine doses needed, duration since last vaccine, or any combination therefor.

5. The computerized-method of claim 1 wherein the vaccine screener requirement includes verifying the vaccine card of a user associated with the arrival event.

6. The computerized-method of claim 1 further comprising:

receiving, by the processor, from a user an indication that a covid event has occurred; and determining, by the processor, based on a user profile associated with the user, one or more additional users who are close contacts to the user based on logged arrival events for the location.

7. A non-transitory computer program product comprising instructions which, when the program is executed cause a processor to:

receive an arrival event, wherein the arrival event includes a login event at a computer;

determine a location for the arrival event based on one or more data items associated with the arrival event, wherein the one or more data items include location information, wherein determining the location further comprises verifying that the login event is not a remote login by:

checking at least two remote sessions for the login event based on the login time of the login event, the login event not being present in both of the at least two remote session ranges then the respective login event is not a remote login;

determining, by the processor, that a user associated with the computing device of the respective login event is physically present in the facility at the start time of the respective login event; and transmitting, by the processor, a notification to a display of the computing device of the user, wherein the notification is one of a reminder to participate in a health check, an indicator that the user is being counted as physically present in the facility, or any combination thereof;

determine a health policy for the arrival event based on the location and a configuration file, wherein the health policy includes a health screener requirement and a vaccine screener requirement and wherein the configuration file comprises one or more vaccine controls, one or more vaccine expiration controls, one or more case expiration control, or any combination thereof, wherein the one or more vaccine controls comprise restricting collection of vaccine data, placing an incomplete proof of vaccination in a pending state, requiring answering of a negative test questions, require proof of vaccine to be uploaded, automatic removal of vaccine records once approved or any combination, wherein the one or more vaccine expiration controls comprise vaccine expiration period, grace period after vaccine expires to update the vaccine proof, or any combination thereof, wherein one or more case expiration controls comprise a number of days a case is active until automatically expiring, for an arrival event that fails the health policy or the vaccine screener requirement, remotely preventing in real-time, by the processor, access to a computing device associated with the user and presenting a message to a user associated with the arrival event to leave the site associated with the arrival event; and for an arrival event that passes the health policy or the vaccine screener policy, remotely outputting in real-time, by the processor, to the user associated with the arrival event a passing indicator and allowing the user to access to a computing device associated with the user.

8. The non-transitory computer program product of claim 7 wherein the health screener requirement and the vaccine screener requirement are configurable.

9. The non-transitory computer program product of claim 8 wherein configurable parameters for the health screener requirement includes completion of a health attestation form, a completion of an online covid test, a temperature check, or any combination thereof.

10. The non-transitory computer program product of claim 8 wherein configurable parameters for the vaccine screener includes vaccine check needed, number of vaccine doses needed, duration since last vaccine, or any combination therefor.

11. The non-transitory computer program product of claim 7 wherein the vaccine screener requirement includes verifying the vaccine card of a user associated with the arrival event.

12. The non-transitory computer program product of claim 7 further causing the processor to:

receive from a user an indication that a covid event has occurred; and determine based on a user profile associated with the user, one or more additional users who are close contacts to the user based on logged arrival events for the location.

* * * * *